(12) United States Patent
Iwase et al.

(10) Patent No.: US 11,435,352 B2
(45) Date of Patent: Sep. 6, 2022

(54) ANALYSIS METHOD AND β-LACTAM ANTIBIOTIC RESISTANCE EVALUATION METHOD

(71) Applicant: Shimadzu Corporation, Kyoto (JP)

(72) Inventors: Tadayuki Iwase, Tokyo (JP);
Yoshinobu Manome, Tokyo (JP);
Yoshimitsu Mizunoe, Tokyo (JP);
Kouki Fujioka, Tokyo (JP); Yuko Fukuyama, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 161 days.

(21) Appl. No.: 16/275,073

(22) Filed: Feb. 13, 2019

(65) Prior Publication Data
US 2019/0250162 A1   Aug. 15, 2019

(30) Foreign Application Priority Data

Feb. 15, 2018   (JP) ............................. JP2018-025381

(51) Int. Cl.
| G01N 33/573 | (2006.01) |
| G01N 33/569 | (2006.01) |
| C12Q 1/34 | (2006.01) |
| G01N 33/68 | (2006.01) |
| C12Q 1/18 | (2006.01) |

(52) U.S. Cl.
CPC ............. G01N 33/573 (2013.01); C12Q 1/18 (2013.01); C12Q 1/34 (2013.01); G01N 33/56911 (2013.01); G01N 33/6851 (2013.01); G01N 2333/986 (2013.01); G01N 2800/44 (2013.01)

(58) Field of Classification Search
None
See application file for complete search history.

(56) References Cited

U.S. PATENT DOCUMENTS

2009/0203003 A1* 8/2009 Shaw ................. C12N 15/1048
435/6.12

FOREIGN PATENT DOCUMENTS

| EP | 2 816 357 A1 | 12/2014 |
| EP | 2 950 092 A1 | 12/2015 |
| WO | WO 2012/023845 A1 | 2/2012 |

OTHER PUBLICATIONS

Fukuyama, "MALDI Matrix Research for Biopolymers", Mass Spectrometry, vol. 4, A0037, pp. 1-14 (Year: 2015).*

Toth et al., "The role of conserved surface hydrophobic residues in the carbapenemase activity of the class D b-lactamases", Acta Crystallographica Section D: Structural Biology, vol. 73, pp. 692-701 (Year: 2017).*

Nielsen et al., "Lipoprotein nature of Bacillus licheniformis membrane penicillinase", PNAS, vol. 78, pp. 3511-3515 (Year: 1981).*

Nielsen et al. II, "b-Lactamase III of Bacillus cereus 569: Membrane Lipoprotein and Secreted Protein", Biochemistry, vol. 22, pp. 4652-4656 (Year: 1983).*

Fenselau et al., "Identification of β-Lactamase in Antibiotic-Resistant Bacillus cereus Spores" 2008, Appl. Environ. Microbiol., vol. 74, 904-906.

J. E. Camara et al., "Discrimination between wild-type and ampicillin-resistant *Escherichia coli* by matrix-assisted laser desorption/ionization time-of-flight mass spectrometry", 2007, Anal. Bioanal Chem., vol. 389, 1633-1638.

J. Thacker et al., "64th ASMS Conference on Mass Spectrometry and Allied Topics", Jun. 5-9, 2016, TP664.

Extended European Search Report dated Apr. 12, 2019 in Patent Application No. 19156401.2, 9 pages.

Thacker, J. et al., "6. Konference", Retrieved from the Internet: https://www.czechms.org/data/cmsc/abooks/abstractbook_2017.pdf, XP055577945, Mar. 31, 2017, 94 pages.

(Continued)

*Primary Examiner* — Michelle F. Paguio Frising
(74) *Attorney, Agent, or Firm* — Oblon, McClelland, Maier & Neustadt, L.L.P.

(57) ABSTRACT

In an analysis method of the present invention, a compound represented by the following formula (I) as a matrix is mixed into an analysis target sample and the mixture is subjected to matrix-assisted laser desorption ionization mass spectrometry. In the formula (I), R is an alkyl group having 3-11 carbon atoms. The analysis target sample is a substance for which whether or not β-lactamase is contained is to be determined. Analysis targets include, for example, bacteria and an extract from bacteria.

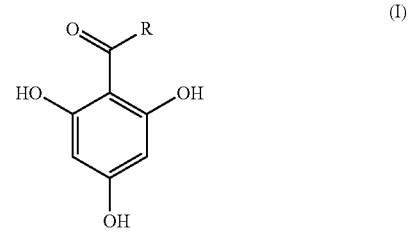

(I)

20 Claims, 4 Drawing Sheets

(56) References Cited

OTHER PUBLICATIONS

Foret, F. et al., "Liquid phase interfacing and miniaturization in matrix-assisted laser desorption/ionization mass spectrometry", Proteomics, XP002526844, vol. 2, No. 4, Apr. 1, 2002, pp. 360-372.
Fukuyama, Y. et al., "Membrane Protein Analyses Using Alkylated Trihydroxyacetophenone (ATHAP) as a MALDI Matrix", Analytical Chemistry, XP055577150, vol. 88, No. 3, Jan. 21, 2016, pp. 1688-1695.
Fukuyama, Y. et al., "Alkylated Trihydroxyacetophenone as a MALDI Matrix for Hydrophobic Peptides", Analytical Chemistry, XP055213897, vol. 85, No. 20, Oct. 15, 2013, pp. 9444-9448.

* cited by examiner

ANALYSIS METHOD AND β-LACTAM ANTIBIOTIC RESISTANCE EVALUATION METHOD

CROSS-REFERENCE TO RELATED APPLICATIONS

The present application is based upon and claims the benefit of priority to Japanese Application No. 2018-025381, filed Feb. 15, 2018, the entire contents of which are incorporated herein by reference.

TECHNICAL FIELD

The present invention relates to an analysis method, and specifically, relates to detection of β-lactamase using matrix-assisted laser desorption ionization mass spectrometry (MALDI-MS). Further, the present invention relates to a method for evaluating β-lactam antibiotic resistance of bacteria.

TECHNICAL BACKGROUND

Due to development of various antibacterial drugs mainly based on antibiotic substances, occurrence of infections of bacteria or the like has remarkably decreased. On the other hand, with mass use of drugs, pathogenic bacteria exhibiting resistance to antibacterial drugs are rapidly increasing. It is known that several types of bacteria exhibit resistance to β-lactam (penicillin and cephalosporin) antibacterial drugs by producing β-lactamase. It is known that β-lactamase is a bacteria-produced enzyme that hydrolyzes and inactivates a β-lactam ring of a β-lactam antibacterial drug and is a water-soluble (hydrophilic) protein.

β-lactamase is in an important position in clinical examination and drug resistance studies. As methods for detecting β-lactamase-producing bacteria, a trace liquid dilution method, a disk diffusion method, a PCR method and the like have been established, but time and cost are required for culturing bacteria and the like. In particular, in a treatment of a bacterial infection or in prevention of an in-hospital infection, it is important to rapidly identify a target and administer an antibiotic substance, and thus, there has been a demand for development of a method capable of more easily detecting β-lactamase-producing bacteria.

Mass spectrometry is a technique capable of detecting and quantifying a target substance contained in a large number of contaminants, and a method has been reported in which, by using mass spectrometry, presence or absence and a molecular weight of a specific substance in bacteria are identified, and a type of the bacteria, drug resistance thereof, and the like are identified. In particular, matrix-assisted laser desorption ionization mass spectrometry (MALDI-MS) is capable of detecting an intact protein and thus has attracted attention as a clinical microbiological examination method capable of identifying bacterial species in a short time. For example, when β-lactamase is detected from bacteria using MALDI-MS, it can be determined that the bacteria are β-lactamase-producing bacteria and exhibit resistance to a β-lactam antibacterial drug. However, reports on analysis of β-lactamase using MALDI-MS have been limited so far (Non-Patent Documents 1-3).

RELATED ART

Non-Patent Documents

[Non-Patent Document 1] C. Fenselau et al., 2008, Appl. Environ. Microbiol., Vol. 74, 904-906.

[Non-Patent Document 2] J. E. Johanna et al., 2007, Anal. Bioanal Chem., Vol. 389, 1633-1638.

[Non-Patent Document 3] J. Thacker et al., ASMS Annual Conference 2016, TP684.

SUMMARY OF THE INVENTION

Problems to be Solved by the Invention

In Non-Patent Document 1, although β-lactamase in spores is analyzed using MALDI-MS, details of experimental protocols including matrix information are not disclosed. In Non-Patent Document 2 and Non-Patent Document 3, by using bacterial species that increase expression of β-lactamase or by using an inducer such as isopropyl-β-thiogalactopyranoside (IPTG), β-lactamase is expressed at a high concentration and extraction and purification of a protein from cultured bacteria are performed, and then analysis using MALDI-MS is performed. In this case, a sinapinic acid (SA) is mainly used as a matrix. For application to clinical examination, it is required that β-lactamase at a low concentration contained in bacteria can be more easily detected with high sensitivity.

Means for Solving the Problems

In view of the above, as a result of examination, the present inventor has found that β-lactamase can be detected with high sensitivity by using MALDI-MS using a specific matrix, and thus accomplished the present invention.

The present invention relates to an analysis method using matrix-assisted laser desorption ionization mass spectrometry (MALDI-MS), a method in which a compound represented by the following formula (I) as a matrix is mixed into an analysis target sample and β-lactamase in the analysis target sample is detected using MALDI-MS.

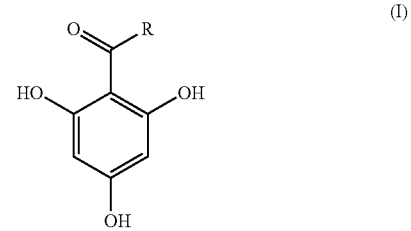

In the formula (I), R is an alkyl group having 3-11 carbon atoms. The number of carbon atoms of R is preferably 5-11, more preferably 5-9, and particularly preferably 7.

The analysis target sample includes, for example, bacteria such as *Escherichia coli*.

Further, the present invention relates to a method for evaluating β-lactam antibiotic resistance of bacteria using MALDI-MS. In the evaluation of β-lactam antibiotic resistance, a compound represented by the above formula (I) as a matrix is mixed into a colony of the bacteria to be evaluated to prepare a mixture of the bacteria and the matrix. The mixture is subjected to matrix-assisted laser desorption ionization mass spectrometry, and an abundance of β-lactamase contained in the bacteria is determined based on an analysis result. When the abundance of β-lactamase exceeds a threshold, it is determined that the bacteria have β-lactam antibiotic resistance.

Effect of the Invention

According to the analysis method of the present invention, β-lactamase contained in bacteria or the like can be detected with high sensitivity using a simple method. By applying the analysis method of the present invention, whether or not bacteria have β-lactam antibiotic resistance can be evaluated.

MODE FOR CARRYING OUT THE INVENTION

Matrix

Figure 1:
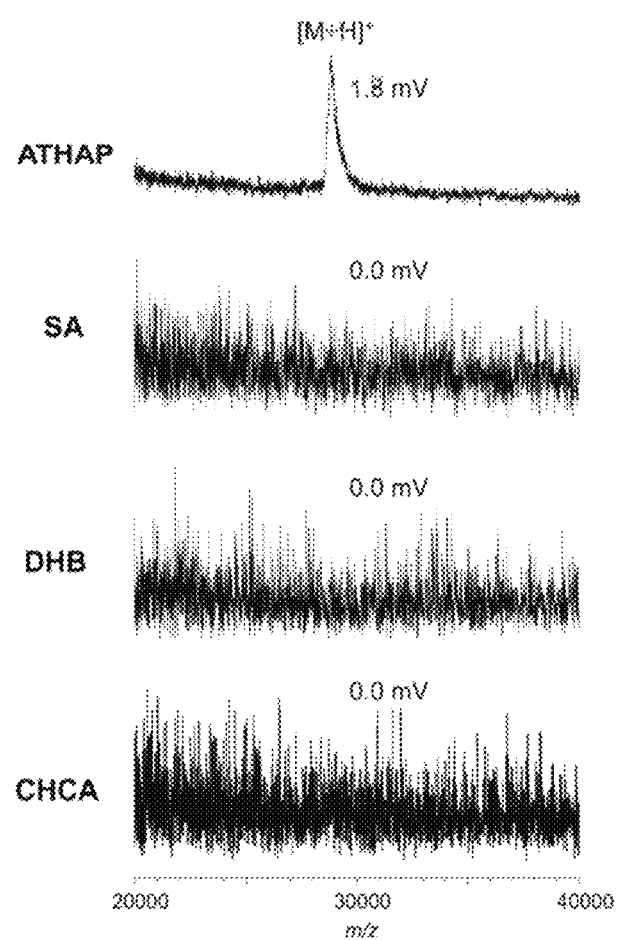
FIG. 1 shows mass spectra of Experimental Example 1 (standard product of β-lactamase).

In the present invention, an analysis target sample is mixed with 2,4,6-trihydroxyphenylalkyl ketone represented by the following formula (I) and analysis using matrix-assisted laser desorption ionization mass spectrometry (MALDI-MS) is performed.

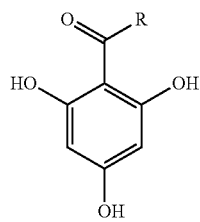

(I)

In the formula (I), R is an alkyl group having 3-11 carbon atoms. Examples of an alkyl group having 3-11 carbon atoms include a propyl group, a butyl group, a pentyl group, a hexyl group, a heptyl group, an octyl group, a nonyl group, a decyl group, and an undecyl group. The alkyl group (R) may be linear or branched. The number of carbon atoms of the alkyl group (R) is preferably 5-11, more preferably 5-9, and particularly preferably 7. That is, a particularly preferable matrix used in the present invention is 1-(2,4,6-trihydroxyphenyl) octane-1-one in which R in formula (I) is a heptyl group.

The above compound is preferably mixed with a solvent to be used as a matrix solution. A concentration of the above compound in a matrix solution may be, for example, from 1 mg/mL to a saturation concentration. Even a smaller concentration within this range can contribute to improving detection sensitivity of β-lactamase. The concentration of the above compound in the matrix solution is preferably about 1-30 mg/mL.

Analysis Target Sample

A mass spectrometry target sample is a sample for which determination of whether or not β-lactamase is contained is required or quantification of a content of β-lactamase is required. β-lactamase is classified into a class A (penicillinase), a class B (carbapenemase), a class C (cephalosporinase) and a class D (oxasilnase) based on a substrate specificity and an amino acid sequence (Ambler classification). Since an intact molecule is detected using MALDI-MS, the present invention is applicable to any one of the classes of β-lactamase.

A typical example of a sample for which determination of whether or not β-lactamase is contained is required is bacteria. Bacteria containing β-lactamase possess a β-lactamase-encoding gene on plasmid or chromosome and exhibit β-lactam antibiotic resistance. Originally, there are very few bacterial species that express β-lactamase. However, bacteria acquire β-lactamase expression by mutation of chromosomal DNA and propagation of plasmids. Both Gram-positive bacteria and Gram-negative bacteria can be analysis targets of the present invention.

Examples of gram-positive bacteria include: *Listeria monocytogenes, Listeria welshimeri, Staphylococcus aureus, Staphylococcus epidermidis, Staphylococcus saprophyticus, Staphylococcus lugdunensis, Staphylococcus schleiferi, Staphylococcus caprae, Streptococcus pneumoniae, Streptococcus viridans, Streptococcus pyogenes, Streptococcus agalactiae, Enterococcus faecalis, Enterococcus faecium, Bacillus licheniformis, Bacillus subtilis, Bacillus anthracis, Bacillus cereus, Bacillus thuringiensis, Bacillus larvae, Mycobacterium tuberculosis, Mycobacterium bovis, Mycobacterium leprae, Mycobacterium ulcerans, Mycobacterium kanasasii, Mycobacterium avium, Mycobacterium paratuberculosis, Mycobacterium scrofulaceam, Mycobacterium microti, Mycobacterium africanum, Mycobacterium canettii, Mycobacterium intracellulare, Mycobacterium simiae, Mycobacterium szulgai, Mycobacterium xenopi, Mycobacterium fortuitum, Mycobacterium chelonei, Mycobacterium marinum, Nocardia asteroids*, and *Rhodococcus equi*.

Examples of Gram-negative bacteria include: *Neisseria gonorrhoeae, Neisseria meningitides, Moraxella catarrhalis, Hemophilus influenzae, Klebsiella pneumoniae, Legionella pneumophila, Pseudomonas aeruginosa, Pseudomonas putida, Escherichia coli, Proteus mirabilis, Enterobacter cloaceae, Serratia marcescens, Helicobacter pylori, Salmonella enteritidis, Salmonella typhi*, and the like.

In the present invention, bacteria can be used directly as they are as an analysis target sample. When bacteria are used as an analysis target, for example, analysis using MALDI-MS is performed by mixing a bacterial culture colony with a matrix. A colony of bacteria may be smeared directly as it is to an MALDI plate, or added dropwise to an MALDI plate after suspending and mixed with a matrix on the MALDI plate. Further, it is also possible that a colony of bacteria and a matrix are mixed with each other and then the mixture is added dropwise to an MALDI plate.

It is also possible that an extract from bacteria is used as a sample for analysis. For example, a protein extracted by lysing bacteria may be used as an analysis target. Further, a sample obtained by purifying an extract from bacteria using a column or the like may be used as a sample for analysis.

In analyzing an extract from bacteria, as compared to analyzing the bacteria directly as they are, types and amounts of impurities contained in the sample are reduced, and thus, analysis with higher sensitivity becomes possible. On the other hand, when bacterial cells are used directly as they are, whether or not β-lactamase is contained in an analysis target, in other words, whether or not the bacteria exhibit β-lactam antibiotic resistance, can be analyzed in a shorter time and at a lower cost.

In the present invention, by using 2,4,6-trihydroxyphenyl alkyl ketone represented by the above formula (I) as a matrix, in addition to being able to detect β-lactamase at a low concentration by using MALDI-MS, β-lactamase can be detected with high sensitivity even when a large number of contaminants are contained in a sample. Therefore, even when bacteria are analyzed directly as they are without performing an extraction or purification operation of a protein from the bacteria, β-lactamase in the bacteria can be detected.

Although why the detection sensitivity of β-lactamase using MALDI-MS is improved by using 2,4,6-trihydroxyphenyl alkyl ketone as a matrix is not clear, one reason is presumed to be that selective ionization of β-lactamase is promoted. It has been reported that 2,4,6-trihydroxyphenyl alkyl ketone represented by the formula (I) is highly effective mainly for enhancing ionization ability of a hydrophobic peptide or a hydrophobic protein (for example, International Publication No. WO 2014/136779). It is known that β-lactamase is generally a water-soluble (hydrophilic) protein. However, it is thought that there is a possibility that, for example, hydrophobic amino acid residues, some hydrophobic sites, hydrophobic regions in higher order structures, and the like exhibit interaction with the hydrophobic 2,4,6-trihydroxyphenylalkyl ketone, and thereby, ionization is promoted.

Analysis Method

The analysis method of the present invention can be executed in the same manner as a common analysis method using MALDI-MS, except that the above analysis target sample and matrix are used. A mass spectrometer is not particularly limited as long as the mass spectrometer is combined with a MALDI (matrix-assisted laser desorption ionization) ion source. Examples of the mass spectrometer include a MALDI-TOF (matrix-assisted laser desorption ionization-time of flight) type mass spectrometer, a MALDI-IT (matrix-assisted laser desorption ionization-ion trap) type mass spectrometer, a MALDI-IT-TOF (matrix-assisted laser desorption ionization-ion trap-time of flight) type mass spectrometer, a MALDI-FTICR (matrix-assisted laser desorption ionization-Fourier transform ion cyclotron resonance) type mass spectrometer, and the like.

In MALDI-MS, first, a mixture of an analysis target sample and a matrix is prepared on a target plate. An analysis target sample and a matrix may be mixed in advance and added dropwise onto a target plate, or, an analysis target sample and a matrix may be added dropwise onto the same place on a target plate and mixed on the target plate (on-target mix method). In the case of the on-target mix method, an order of adding dropwise the analysis target sample and the matrix is arbitrary, and the two may be both added dropwise at the same time.

As described above, a matrix is preferably mixed with a solvent and used as a matrix solution. As the solvent, acetonitrile (ACN), trifluoroacetic acid (TFA), methanol (MeOH), ethanol (EtOH), tetrahydrofuran (THF), dimethylsufoxide (DMSO), water, mixtures thereof, and the like are preferably used. Examples of mixed solvents include an ACN-TFA aqueous solution, an ACN aqueous solution, MeOH-TFA, an MeOH aqueous solution, an EtOH-TFA aqueous solution, an EtOH aqueous solution, a THF-TFA aqueous solution, a THF aqueous solution, a DMSO-TFA aqueous solution, a DMSO aqueous solution, and the like. A solvent may be added to a mixture of a matrix and an analysis target sample.

A volume of a mixture of an analysis target sample and a matrix on a target plate (a volume including a solvent) is, for example, about 0.1 µL-2 µL. Before performing mass spectrometry, it is preferable to remove the solvent from the mixture on the target plate. The removal of the solvent may be performed, for example, by natural drying or the like.

The mixture of the analysis target sample and the matrix is subjected to MALDI-MS to obtain mass spectra as an analysis result. Based on the analysis result, whether or not β-lactamase is contained in the analysis target sample can be determined. That is, when a peak is confirmed at m/z corresponding to a molecular weight (generally about 20,000-42,000 Da) of β-lactamase to be detected, it can be determined that β-lactamase is contained in the analysis target sample. Although the molecular weight of β-lactamase varies depending on a type, whether or not a detected peak is due to β-lactamase can be confirmed by collating with a database or the like. Many types of β-lactamases have a molecular weight of 20,000-42,000 Da, and, when these β-lactamases are contained in a sample, a mass spectrum peak is confirmed at m/z in a range of 20,000-42,000. The method of the present invention using 2,4,6-trihydroxyphenyl alkyl ketone as a matrix is particularly suited for high sensitivity detection of β-lactamase showing a peak at m/z in a range of 20,000-42,000.

When a peak derived from β-lactamase is confirmed in MALDI-MS mass spectra of bacteria or an extract from the bacteria, it can be determined that the bacteria to be analyzed contain β-lactamase and exhibit β-lactam antibiotic resistance. That is, in evaluating β-lactam antibiotic resistance, an abundance of β-lactamase in bacteria to be evaluated can be obtained based on a peak derived from β-lactamase in mass spectra.

When the abundance of β-lactamase in the bacteria exceeds a predetermined threshold, it can be determined that the bacteria to be evaluated have β-lactam antibiotic resistance.

Further, the type of the β-lactamase can be identified based on a spectral shape of the mass spectra and a value of the m/z. Identification of the type of the β-lactamase may also be performed by collating with a database. Further, identification of β-lactam-resistant bacteria may also be performed based on the obtained mass spectra.

EXAMPLES

In the following Experimental Examples, a standard product solution sample of TEM-1 type β-lactamase (about 29,000 Da) classified as Class A (0.48 mg/mL; Thermo Fisher Scientific Co., Ltd., PV 3575) was used and mixed with various matrices, and analysis using MALDI-MS was performed.

Experimental Example 1

As a matrix solution, a 50% ACN and 0.1% TFA solution of 1-(2,4,6-trihydroxyphenyl) octan-1-one (alkylated trihydroxyacetophenone: ATHAP; NARD Inc.) (10 mg/mL) was prepared. As matrix solutions to be compared, 50% ACN and 0.1% TFA solutions were respectively prepared for a sinapinic acid (SA; Laser Bio Inc.), an α-cyano-4-hydroxycinnamic acid (CHCA; Laser Bio Inc.) and a 2,5-dihydroxybenzoic acid (DHB; Laser Bio Inc.).

0.5 µL of a β-lactamase standard product solution was added dropwise onto a well of a target plate and then 0.5 µL of the above matrix solution was added dropwise (on-target mix method), and, after drying the solvent, sample/matrix mixed crystals were analyzed in a linear mode and a positive ion mode of AXIMA Performance (registered trademark) (Shimadzu Corporation). Mass spectra are shown in FIG. 1.

Experimental Example 2

A β-lactamase standard product solution sample was purified using Zip Tip C18 (Merck Millipore Inc.) and was eluted with a 50% ACN and 0.1% TFA solution. A sample obtained after the purification was serially diluted with a 50% ACN and 0.1% TFA solution to prepare sample solutions respectively having β-lactamase concentrations of 16 pmol/µL, 1.6 pmol/µL, 0.16 pmol/µL and 0.016 pmol/µL.

Figure 2:
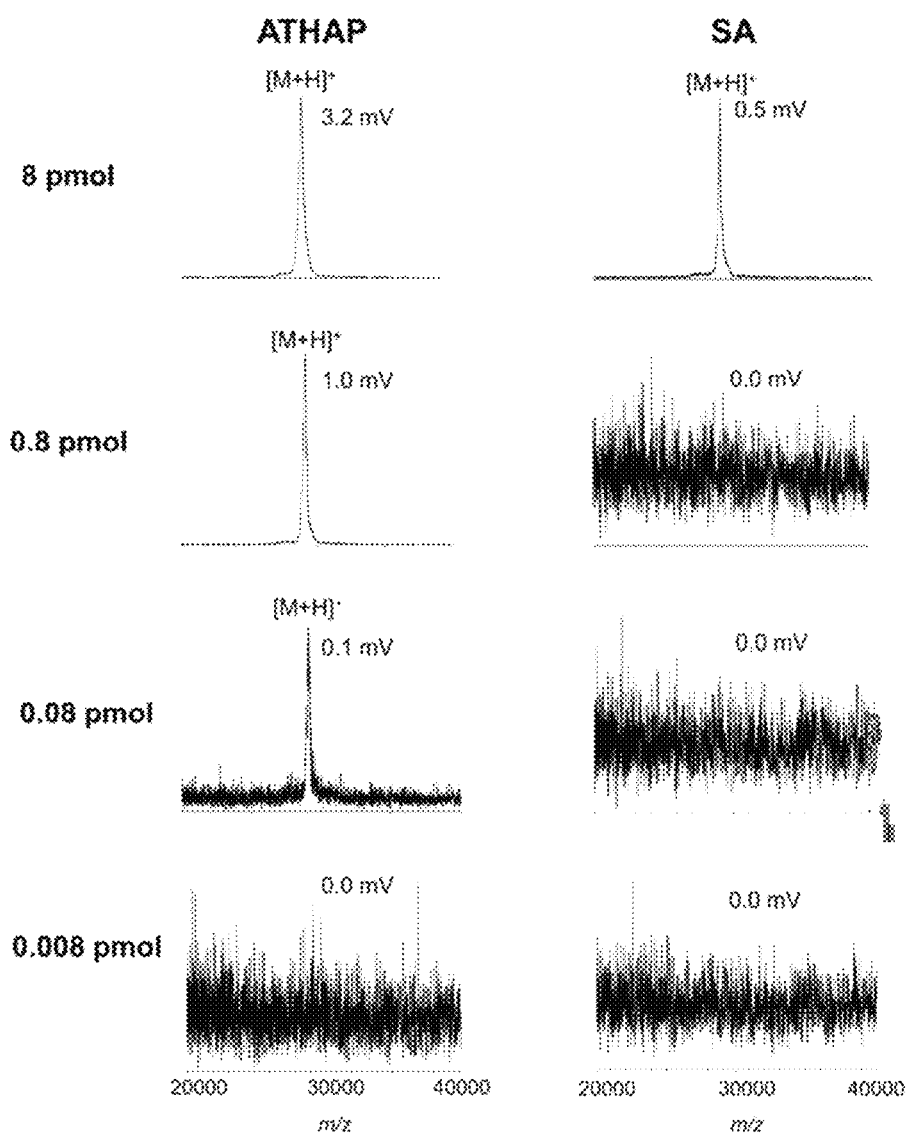
FIG. 2 shows mass spectra of Experimental Example 2 (purified product of β-lactamase).

As matrix solutions, ATHAP and SA prepared in the same manner as in Example 1 were used. Sample/matrix mixed crystals obtained using on-target mix in the same manner as in Experimental Example 1 were analyzed using MALDI-MS. Mass spectra are shown in FIG. 2. A left side of FIG. 2 shows an amount of β-lactamase contained in one well. This also applies to FIG. 3 and FIG. 4 to be described later.

Experimental Example 3

After ethanol for storage was evaporated and dried, *B. subtilis* was suspended in 20 µL of a formic acid.

Figure 3:
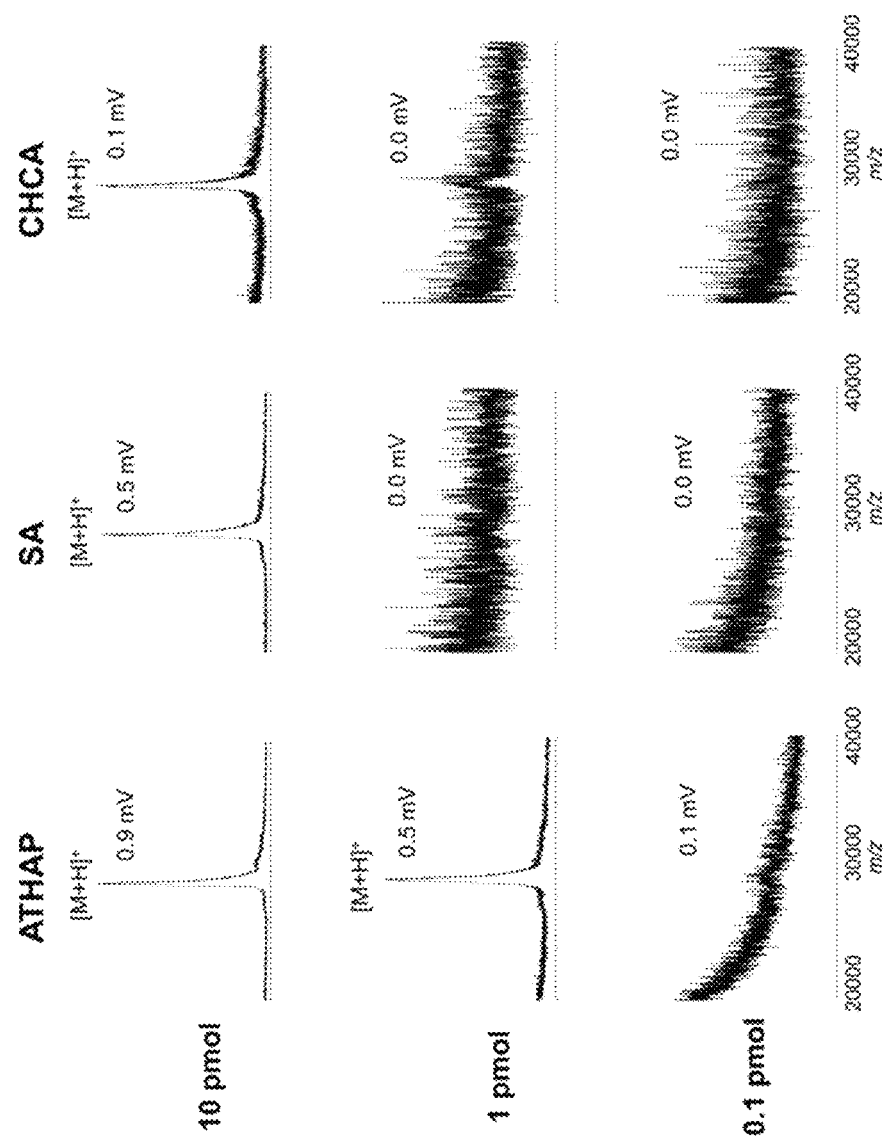
FIG. 3 shows mass spectra of Experimental Example 3 (mixture of a purified product of β-lactamase and *B. subtilis*)

Similar to Experimental Example 2, a β-lactamase standard product solution was purified using Zip Tip C18 and serially diluted to prepare sample solutions respectively having β-lactamase concentrations of 20 pmol/µL, 2 pmol/µL, and 0.2 pmol/µL. As matrix solutions, ATHAP, SA and CHCA prepared in the same manner as in Example 1 were used. 0.5 µL of a concentration-adjusted β-lactamase solution was added dropwise onto a target plate, and thereafter, 0.5 µL of the above-described bacterial suspension was added dropwise. After the solvent is dried, 1 µL of the matrix was added dropwise, and the sample/matrix mixed crystals obtained after drying the solvent were analyzed using MALDI-MS. Mass spectra are shown in FIG. 3.

Experimental Example 4

Figure 4:
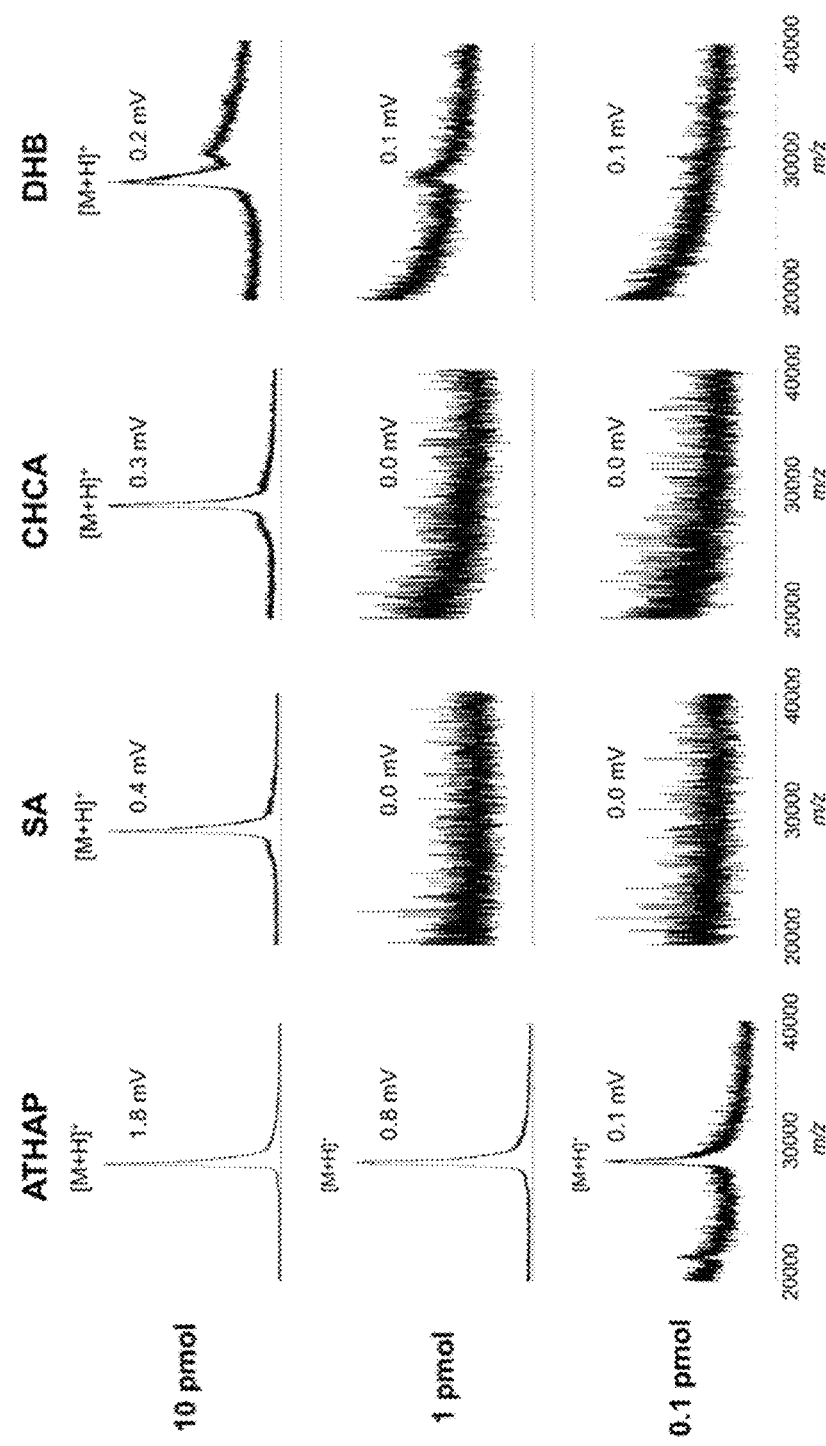
FIG. 4 shows mass spectra of Experimental Example 4 (mixture of a purified product of β-lactamase and *S. epidermidis*).

Analysis using MALDI-MS was performed using four kinds of matrices including ATHAP, SA, CHCA and DHB in the same manner as in Experimental Example 3 except that *S. epidermidis* was used instead of *B. subtilis*. Mass spectra are shown in FIG. 4.

Evaluation of Results of Experimental Examples

From the results shown in FIG. 1, it is clear that, by using ATHAP as a matrix, it is possible to detect, with high sensitivity, a peak of β-lactamase which was difficult to detect using the other three types of matrices.

As shown in FIG. 2, in Experimental Example 2 in which the β-lactamase purified using Zip Tip was used as an analysis target sample, even when SA is used as a matrix, 8 pmol of β-lactamase was detected, and the detection result of β-lactamase using MALDI-MS in above-described Non-Patent Document 2 and Non-Patent Document 3 was reproduced. When SA was used as a matrix, 0.8 pmol or less of β-lactamase was not detected, whereas when ATHAP was used as a matrix, 0.08 pmol of β-lactamase ions were detected. From this result, it is clear that detection sensitivity of β-lactamase was improved by 100 times (as a detection limit) by using ATHAP as a matrix as compared to SA.

As shown in FIGS. 3 and 4, even in Experimental Example 3 and Experimental Example 4, in which a sample obtained by mixing a bacterial suspension and β-lactamase was analyzed, similar to Experimental Examples 1 and 2, by using ATHAP as a matrix, detection sensitivity was greatly improved (by 10-100 times as a detection limit) as compared to using other matrices.

As shown by the above results, by using 2,4,6-trihydroxyphenyl alkyl ketone as an MALDI matrix, even in the presence of contaminants contained in bacteria and the like, detection sensitivity of β-lactamase is improved. That is, according to the present invention, even when bacteria are used as an analysis target sample, β-lactamase contained in the bacteria can be detected with high sensitivity, and whether or not the bacteria exhibit β-lactam antibiotic resistance can be determined.

What is claimed is:

1. An analysis method for detecting β-lactamase in an analysis target sample, comprising:
    mixing a compound of formula (I)

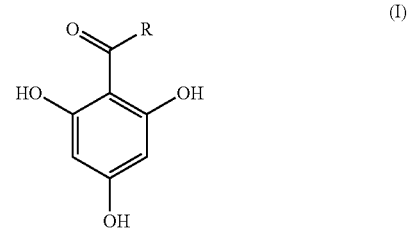

as a matrix into the analysis target sample including at least one of bacteria and a colony of the bacteria; and
    subjecting a mixture comprising the compound of formula (I) and the analysis target sample including at least one of bacteria and the colony of the bacteria directly to matrix-assisted laser desorption ionization mass spectrometry such that the β-lactamase in the bacteria of the analysis target sample is detected,
    wherein in the formula (I), R is an alkyl group having 3-11 carbon atoms.

2. The analysis method according to claim 1, wherein the analysis target sample is the bacteria.

3. The analysis method according to claim 2, wherein the matrix is a matrix solution comprising a solvent and the compound of formula (I) such that a concentration of the compound of formula (I) is in a range of 1 mg/mL to a saturation concentration.

4. The analysis method according to claim 2, wherein the matrix is a matrix solution comprising a solvent and the compound of formula (I) such that a concentration of the compound of formula (I) is in a range of 1 mg/mL to 30 mg/mL.

5. The analysis method according to claim 1, further comprising:
    determining an abundance of β-lactamase contained in the analysis target sample based on an analysis result; and
    determining that the analysis target sample has β-lactam antibiotic resistance when the abundance of β-lactamase exceeds a threshold,
    wherein the analysis target sample includes the bacteria such that the determining of the abundance of β-lactamase comprises determining the abundance of β-lactamase contained in the bacteria.

6. The analysis method according to claim 5, wherein the matrix is a matrix solution comprising a solvent and the compound of formula (I) such that a concentration of the compound of formula (I) is in a range of 1 mg/mL to a saturation concentration.

7. The analysis method according to claim 5, wherein the matrix is a matrix solution comprising a solvent and the compound of formula (I) such that a concentration of the compound of formula (I) is in a range of 1 mg/mL to 30 mg/mL.

8. The analysis method according to claim 1, wherein the analysis target sample includes the bacteria.

9. The analysis method according to claim 1, wherein the β-lactamase is a hydrophilic β-lactamase.

10. The analysis method according to claim 1, wherein the matrix is a matrix solution comprising a solvent and the compound of formula (I) such that a concentration of the compound of formula (I) is in a range of 1 mg/mL to a saturation concentration.

11. The analysis method according to claim 10, wherein the solvent is at least one solvent selected from the group consisting of acentonitrile, trifluoroacetic acid, methanol, ethanol, tetrahydrofuran, dimethylsufoxide and water.

12. The analysis method according to claim 1, wherein the matrix is a matrix solution comprising a solvent and the compound of formula (I) such that a concentration of the compound of formula (I) is in a range of 1 mg/mL to 30 mg/mL.

13. The analysis method according to claim 12, wherein the solvent is at least one solvent selected from the group consisting of acentonitrile, trifluoroacetic acid, methanol, ethanol, tetrahydrofuran, dimethylsufoxide and water.

14. The analysis method according to claim 1, further comprising:
adding a solvent to the mixture comprising the compound of formula (I) and the analysis target sample such that a concentration of the compound of formula (I) is in a range of 1 mg/mL to a saturation concentration.

15. The analysis method according to claim 1, further comprising:
adding a solvent to the mixture comprising the compound of formula (I) and the analysis target sample such that a concentration of the compound of formula (I) is in a range of 1 mg/mL, to 30 mg/mL.

16. The analysis method according to claim 1, wherein a concentration of the β-lactamase in the analysis target sample is 1 pmol or less.

17. The analysis method according to claim 1, wherein a concentration of the β-lactamase in the analysis target sample is 0.8 pmol or less.

18. A method for evaluating β-lactam antibiotic resistance of bacteria, comprising:
mixing a compound of formula (I)

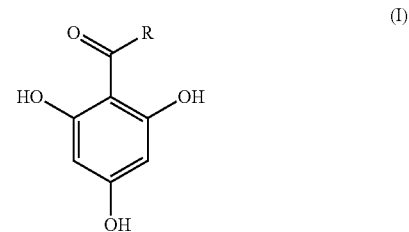

as a matrix to a colony of the bacteria such that a mixture comprising the bacteria to be evaluated and the matrix is prepared;
subjecting the mixture comprising the bacteria and the matrix directly to matrix-assisted laser desorption ionization mass spectrometry such that β-lactamase in the bacteria is detected;
determining an abundance of the β-lactamase contained in the bacteria based on an analysis result; and
determining that the bacteria have β-lactam antibiotic resistance when the abundance of β-lactamase exceeds a threshold,
wherein in the formula (I), R is an alkyl group having 3-11 carbon atoms.

19. The method according to claim 18, wherein the matrix is a matrix solution comprising a solvent and the compound of formula (I) such that a concentration of the compound of formula (I) is in a range of 1 mg/mL to a saturation concentration.

20. The method according to claim 18, wherein the matrix is a matrix solution comprising a solvent and the compound of formula (I) such that a concentration of the compound of formula (I) is in a range of 1 mg/mL to 30 mg/mL.

* * * * *